United States Patent [19]

Croce

[11] Patent Number: 4,701,409
[45] Date of Patent: Oct. 20, 1987

[54] DETECTION OF B-CELL NEOPLASMS

[75] Inventor: Carlo M. Croce, Philadelphia, Pa.

[73] Assignee: The Wistar Institute, Philadelphia, Pa.

[21] Appl. No.: 671,580

[22] Filed: Nov. 15, 1984

[51] Int. Cl.[4] .................. C12Q 1/68; C12P 19/34; C12N 15/00
[52] U.S. Cl. .......................... 435/6; 435/91; 435/172.3; 935/9
[58] Field of Search ............... 435/6, 68, 91, 172.3; 935/76, 77, 78

[56] References Cited

U.S. PATENT DOCUMENTS 4,535,058  8/1985  Weinberg et al. ............ 435/6
4,582,788  4/1986  Erlich ......................... 435/6

OTHER PUBLICATIONS

Tsujimoto et al, "Clustering of Breakpoints on Chromosome II in Human B-Cell Neoplasms with the t(11,14) Chromosome Translocation", Nature, vol. 315, pp. 340-343 (1985).
Tsujimoto et al, "The t(14;18) Chromosome Translocations Involved in B-Cell Neoplasms Result from Mistakes in VDJ Joining", Science, vol. 229, pp. 1390-1393 (1985).
Tsujimoto et al, "Involvement of the bcl-2 Gene in Human Follicular Lymphoma", Science, vol. 228, pp. 1440-1443, (1985).
Yunis et al., (1982), New Eng. J. Med. 307: 1231-1236.
Dalla-Favera et al., (1982), Proc. Natl. Acad. Sci. USA 79:7824-7827.
Taub et al., (1982), Proc. Natl. Acad. Sci. USA 79: 7837-7841.
Neel et al., (1982), Proc. Natl. Acad. Sci. USA 79: 7842-7846.
Croce et al., (1983), Proc. Natl. Acad. Sci. USA 80: 6922-6926.
Erikson et al., (1983), Proc. Natl. Acad. Sci USA 80: 7581-7585.
Croce et al., (1984), Proc. Natl. Acad. Sci. USA 81: 3170-3174.
Tsujimoto et al., (1984), Science 224: 1403-1406.
Erikson et al., (1984), Proc. Natl. Acad. Sci. USA 81: 4144-4148.
Tsujimoto et al., (1984), Science (in press).
Pegoraro et al., (1984), Proc. Natl. Acad. Sci. USA (in press).

Primary Examiner—Thomas G. Wiseman
Assistant Examiner—Thomas D. Mays
Attorney, Agent, or Firm—Banner, Birch, McKie & Beckett

[57] ABSTRACT

B-cell neoplasm is detected by hybridizing lymphocytic DNA with DNA probes that identify chromosomal translocations between human chromosomes 11 and 18.

7 Claims, 5 Drawing Figures

4,701,409

DETECTION OF B-CELL NEOPLASMS

BACKGROUND OF THE INVENTION

The invention described herein was made in the course of work under a grant or award from the Department of Health, Education and Welfare.

A favorable prognosis for a cancer is dependent upon the early detection of malignant cells. B-cell neoplasms, such as lymphocytic leukemias, follicular lymphomas, and others, develop from aberrant cells which have chromosomal translocations. Karyologic analyses of neoplastic B-cells indicate that they carry chromosomal translocations characteristic of a particular neoplasm (See Erikson et al., *Proc. Nat'l Acad. Sci. USA* 80: 4822–4826 (1983), and *Proc. Nat'l. Acad. Sci. USA* 81: 4144–1448 (1984)). For example, a translocation between chromosomes 14 and 18 is characteristic of human follicular lymphomas (See Croce et al., *Proc. Nat'l Acad. Sci. USA* 80: 6922–6926 (1983), and Yuni et al., *N. Engl. J. Med.* 307: 1231–1236 (1982)).

Karyologic analysis of lymphocytes, however, is not an efficient technique for screening large numbers of individuals to detect chromosomal rearrangements of these B-cell neoplasms. There is, thus, a need for a facile test for the diagnosis of suspected B-cell neoplasms.

SUMMARY OF THE INVENTION

It is one object of this invention to provide a test to detect and identify chromosomal translocations in B-cell neoplasms.

It is another object of this invention to provide a DNA probe which can detect the presence of hybrid chromosomes produced by a translocation.

In accordance with this invention, there is provided a method for diagnosing B-cell neoplasm comprising hybridizing a labeled DNA probe to restricted B-cell DNA, said DNA probe hybridizing to a region of DNA lying between a restriction site of a hybrid chromosome of a malignant B-cell and the breakpoint of said chromosome, said restriction site being unique to said region; identifying the pattern of restricted chromosomal DNA fragments to which said DNA probe hybridizes; and detecting differences between the test pattern and the pattern for restricted normal chromosomal DNA.

The DNA probes used in this invention identify gene loci located on translocated chromosomes that are involved in the malignant transformation of B-cells. The invention permits the detection and identification of B-cell neoplasms, such as follicular lymphoma, diffuse B-cell lymphoma and others, in patients in the early stage of the disease. The invention does not require manifestation of overt symptoms for an accurate diagnosis.

DETAILED DESCRIPTION OF THE INVENTION

Figure 1:
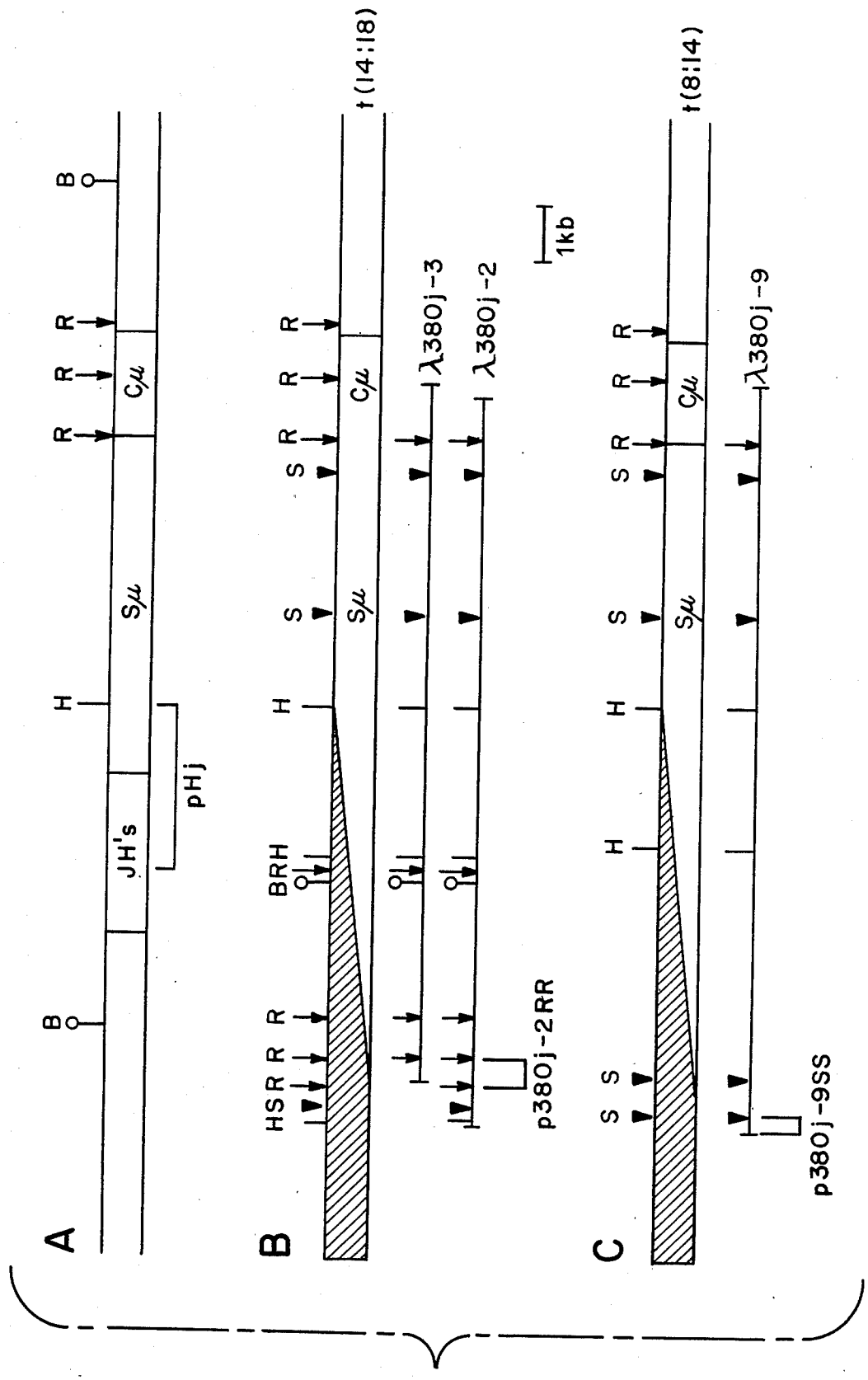
FIG. 1 depicts restriction maps of the germ line C-mu gene (A) and of the two classes of recombinant clones from the 14q+ chromosomes resulting from the t(14;18) (B) and the t(8;14) (C) translocations.

The DNA probes contemplated for use in this invention may be derived from the DNA of B-cell lines maintained in vitro which carry chromosomal translocations or from fresh samples obtained directly from patients with B-cell neoplasms. A full genomic library may be prepared from DNA of these cell lines. Any of the known techniques for constructing genomic libraries may be employed. Such procedures include, without limitation, partially digesting genomic DNA with a restriction enzyme, purifying DNA fragments 15 to 25 kb in length, ligating the fragments with DNA of a lambda phage vector, and packaging in vitro.

The desired fragments of DNA can be obtained by screening independent recombinant phages with a probe specific for a gene sequence located near the breakpoint of the hybrid chromosome present in the B-cell line, or in the fresh neoplastic cells. On chromosome 14, for example, the immunoglobin heavy chain gene lies near the breakpoint. On chromosome 22, the immunoglobin lambda chain gene lies near the breakpoint and the kappa chain immunoglobin gene lies near the breakpoint of chromosome 2. The c-myc oncogene lies near the breakpoint of chromosome 8.

The term breakpoint, also referred to as the joining region, as used herein refers to the locus at which the covalent bonds between the nucleotides, comprising the DNA backbone, break and reform with nucleotides derived from a different chromosome. The chromosome thus formed is a hybrid chromosome consisting of DNA derived from more than one chromosome. Translocations involving chromosomes 14 and 18 have been observed in the great majority of follicular lymphomas. Other translocations, which occur in B-cell neoplasms, involving chromosome 8 with 2, 8 with 14, 8 with 22, and 11 with 14, are also known.

A B-cell carrying a translocation has two hybrid chromosomes: a hybrid chromosome which appears by karyotypic analysis to be longer than its homolog, and a hybrid chromosome which, by karyotypic analysis, appears shorter than its homolog. The term hybrid chromosome as used herein is generic to any chromosome comprised of DNA from more than one chromosome.

DNA derived from the chromosome region spanning the breakpoint of a hybrid chromosome has a restriction map that differs from germ line DNA and can thus be identified by restriction map analysis. For example, a DNA clone, derived from a normal chromosome 14 which spans the breakpoint has a characteristic restriction map when cut with a restriction enzyme or enzymes. A DNA clone, derived from a hybrid chromosome 14, which spans the breakpoint and thus includes DNA sequences from chromosome 14 and another chromosome, such as chromosome 18, has a different restriction map when cut with the same restriction enzyme or enzymes because the nucleotide sequence of this DNA clone differs from the sequence of the nucleotides of the clone derived from the normal chromosome 14. A restriction map represents the pattern of DNA fragments of specific sizes which result when a DNA segment is cut with a restriction enzyme or several restriction enzymes. Restriction enzymes, which recognize and cut at specific DNA sequences are known in the art and include, without limitation, enzymes such as EcoRI, Hind III, and Sau3a, which are purified from microorganisms.

The DNA spanning the breakpoint may be subcloned and processed to select a DNA probe that hybridizes to ony one side of the breakpoint. That is, it is purified and cut with the desired restriction enzyme to produce DNA fragments which are then cloned into a plasmid vector and propagated in a microorganism. DNA isolated from the subclones may be hybridized to DNA derived from hybrid cells (for example, rodent×human cells) containing only one human chromosome such as chromosome 14 and also hybridized to hybrid cells containing a different human chromosome, such as chromosome 18. Subclones which hybrize to the DNA from cells containing human chromosome 18 but not to the DNA from cells containing human chromosome 14 may be selected. Alternatively, subclones which hybridize to chromosome 14 but not to 18 may be selected. Those subclones, which contain DNA homologous to chromosomal DNA on only one side of the breakpoint, are the DNA probes contemplated for use in this invention. As is evident, this invention contemplates use of a DNA probe that hybridizes to DNA lying on either side of the breakpoint. The size of a DNA probe can vary from approximately 20 nucleotides to approximately hundreds or thousands nucleotides.

The cell lines contemplated for use in this invention are derived from malignant B-cells which have chromosomal translocations. Such cell lines include but, are not limited to, chronic lymphocytic leukemia, follicular lymphoma, diffuse B-cell lymphoma, and other leukemias or lymphomas. Such cells may be cultured by employing standard techniques known to those skilled in the art.

The above is a representative procedure by which the DNA probes of this invention may be obtained. Other procedures known in the art may also be employed.

Any source of B-cells is suitable for use in the diagnostic test of this invention. The diagnostic test, for example, may employ a sample of peripheral blood obtained from an individual who is being screened for the presence of B-cell neoplasm. DNA is purified from the lymphocytes employing standard techniques well known to those skilled in the art. Aliquots of lymphocyte DNA are each incubated with a restriction enzyme or enzymes. A restriction enzyme is chosen so that when the DNA of the chromosome is cut with this restriction enzyme the probe hybridizes to a region of DNA lying between the breakpoint of the chromosome and the DNA sequence at which the selected restriction enzyme cuts. This DNA region thus contains a unique site for this restriction enzyme. The probe may also hybridize to a DNA sequence beyond the restriction site. Selection of an appropriate restriction enzyme is well within the skill of the art.

The restricted DNA samples may be separated by agarose gel electrophoresis and blotted to nitrocellulose filters, essentially as described by Southern (Erikson, et al., Proc. Nat'l Acad. Sci. 80: 7581–7585 (1983)). Other procedures for separating restricted DNA fragments and transferring them to an appropriate substrate for further processing may also be employed.

The separated areas of DNA on the nitrocellulose filters or on other appropriate substrates are hybridized to the labeled DNA probe which is homologous to a region of DNA near a breakpoint of a translocated chromosome in a B-cell line derived from a neoplasm. The hybridization reaction may be carried out under standard conditions, known to those skilled in the art. Thereafter, the separated areas of DNA are examined to determine if hybridization occurred. DNA from a lymphocyte sample which is neoplastic will exhibit a different hybridization pattern than the control DNA because the patterns of hybridization have changed in size or additional pattern(s) of hybridization have appeared which represent hybridization of the probe with fragments derived from the rearranged hybrid chromosome.

Polymorphonisms in the relevant regions have been looked for and have not been found. Accordingly, the normal DNA pattern of a normal cell of any individual can be employed as a standardized control for the test of this invention. If desired, DNA from a normal cell (e.g., a T-cell or any other cell that is not a B-cell) from the individual being tested may be used for a follow-up test if such follow-up test is pursued.

In one typical procedure for the test of this invention, the DNA probe can be labeled, for example, with radioactive phosphorus and DNA from a gel transferred to a solid substrate hybridized with it. The substrate may be washed and dried and the hybridization detected by exposing the dried substrate to X-ray film in order to visualize the results of the test. A lane of the gel which corresponds to a restricted lymphocyte DNA sample that does not carry a neoplasm will exhibit a characteristic pattern of hybridization and will serve as a control lane against which the test DNA is compared. Other means for labeling the DNA probe and detecting hybridization are known to those skilled in the art and may also be employed.

In one embodiment of this invention the test cell DNA is hybridized to a mixture of DNA probes derived from cell lines carrying different translocations. Further screening with separate DNA probes may be conducted if the initial screen yields a positive result.

The following examples are included for illustrative purposes only and are not intended to limit the scope of the invention.

EXAMPLE 1

Peripheral blood was obtained from a 15-year old boy who was diagnosed, based on morphologic examination of peripheral blood and bone narrow smears, as having acute lymphoblastic leukemia type L2 (FAB classification). The data on which this diagnosis is based is summarized in Table 1.

TABLE I

|  | Fresh Cells 1,3 | Cell Line 2,3 |
|---|---|---|
| Cytochemical stains |  |  |
| Periodic acid Schiff | 0 | 0 |
| Peroxidase | 0 | 0 |
| Alkaline phosphatase | 10 | 0 |
| —Naphtyl—acetate-esterase | 12 | 0 |
| Surface markers |  |  |
| Polyvalent immunoglobulin | 2 | 0 |
| SRBC | 2 | 0 |
| Fc receptor | 4 | 0 |
| C3b receptor | 5 | 0 |
| Reactivity with monoclonal antibodies |  |  |

TABLE I-continued

|  | Fresh Cells 1,3 | Cell Line 2,3 |
|---|---|---|
| B33.1 | 81 | 95 |
| J-5 | 80 | 89 |
| OKT-3 | 10 | 0 |
| OKT-4 | 0 | 0 |
| OKT-6 | 1 | 0 |
| OKT-8 | 2 | 0 |
| OKT-11 | 11 | 0 |
| L5-1 | 60 | 72 |
| Intracellular markers | | |
| Nuclear TdT | 92 | 90 |
| Cytoplasmic immunoglobins | 0 | 0 |
| EBNA | 0 | 0 |

[1] Unseparated peripheral blood cells from the patient in relapse (Sept. 1983).
[2] Cell line established from same blood specimen.
[3] Percentage of positive cells.

The blood was mixed 9/1 with 3.4M sodium citrate, layered on Lymphoprep ™ density gradient (1.070 sp density; Meyggard and Co., Oslo, Norway), and centrifuged for removal of erythrocytes and granulocytes. Cells collected from the interface were washed, seeded at $1 \times 10^8$/ml RPMI 1640 medium with 15% fetal calf serum, and incubated at 37° C. in 5% $CO_2$. The cells maintained the ability to grow indefinitely in suspension culture. The cell line derived from the blood sample taken during the boy's relapse is designated cell line 380.

As shown in Table 1, the 380 cells do not express membrane bound immunoglobulins. A strong positive reaction, however, was observed with antibodies directed againt IA-Like antigens (B33.1) and against CALLA, a common acute lymphocytic leukemia antigen (J5). The cells did not react with antibodies specific for T-cell markers (Table 1). No expression of Epstein Barr virus nuclear antigen (EBNA) was detected in the 380 cells. In addition, the cells were negative for the expression of cytoplasmic immumoglobulins, but positive for TdT as determined by immunofluorescence (Table 1). Karyotype analysis of the 380 cells revealed the presence of two reciprocal chromosomal translocations.

The 380 cells have two abnormal chromosomes 14 (14q+), one rearranged chromosome 8 (8q−), and one abnormal chromosome 18 (18q−). One of the 14q+ chromosomes was the result of the translocation of the distal end of a long arm of chromosome 8 to the heavy chain locus on band q32 of chromosome 14, while the other 14q+ chromosome resulted from the translocation of the segment q21→qter of human chromosome 18 to the heavy chain locus. No other abnormality in chromosome morphology was detected in the karyotype.

EXAMPLE 2

In the same manner as Example 1 human leukemic cells, designated CLL 271, derived from a 65-year old male with chronic lymphocytic leukemia (CLL) of the B-cell type, a t(11;14) (q13;q32), chromosonal translocation, were obtained and their DNA was extracted. The cells were also hybridized with mouse myeloma cells and hybrids containing the translocated chromosomes were obtained (Erikson et al., *Proc. Nat'l. Acad. Sci. USA* 81: 4144-4148 (1984)).

EXAMPLE 3

A full genomic library was prepared from the DNA of the 380 cells of Example 1. Genomic DNA was partially digested with the restriction enzyme Sau 3A, and DNA fragments 14 to 23kb in length were purified by sucrose gradient centrifugation. The fragments were then ligated with DNA of the lambda phage vector EMBL3A (Tsjimoto et al., *Science* 224: 1403 (1984)) which was cut with Bam HI. After packaging in vitro in *E. coli*, 420,000 independent recombinant phages were screened with a probe specific for the $J_H$(the H (heavy) chain joining region) DNA segment (pHj) (FIG. 1, H, Hind III; R. Eco RI; S. Sau 3A). Nine recombinant clones were obtained and their restriction map analysis allowed classification into groups that represented sequences derived from the two 14q+ chromosomes. The restriction maps and representative overlapping clones of each group are shown in FIG. 1.

EXAMPLE 4

Figure 2:
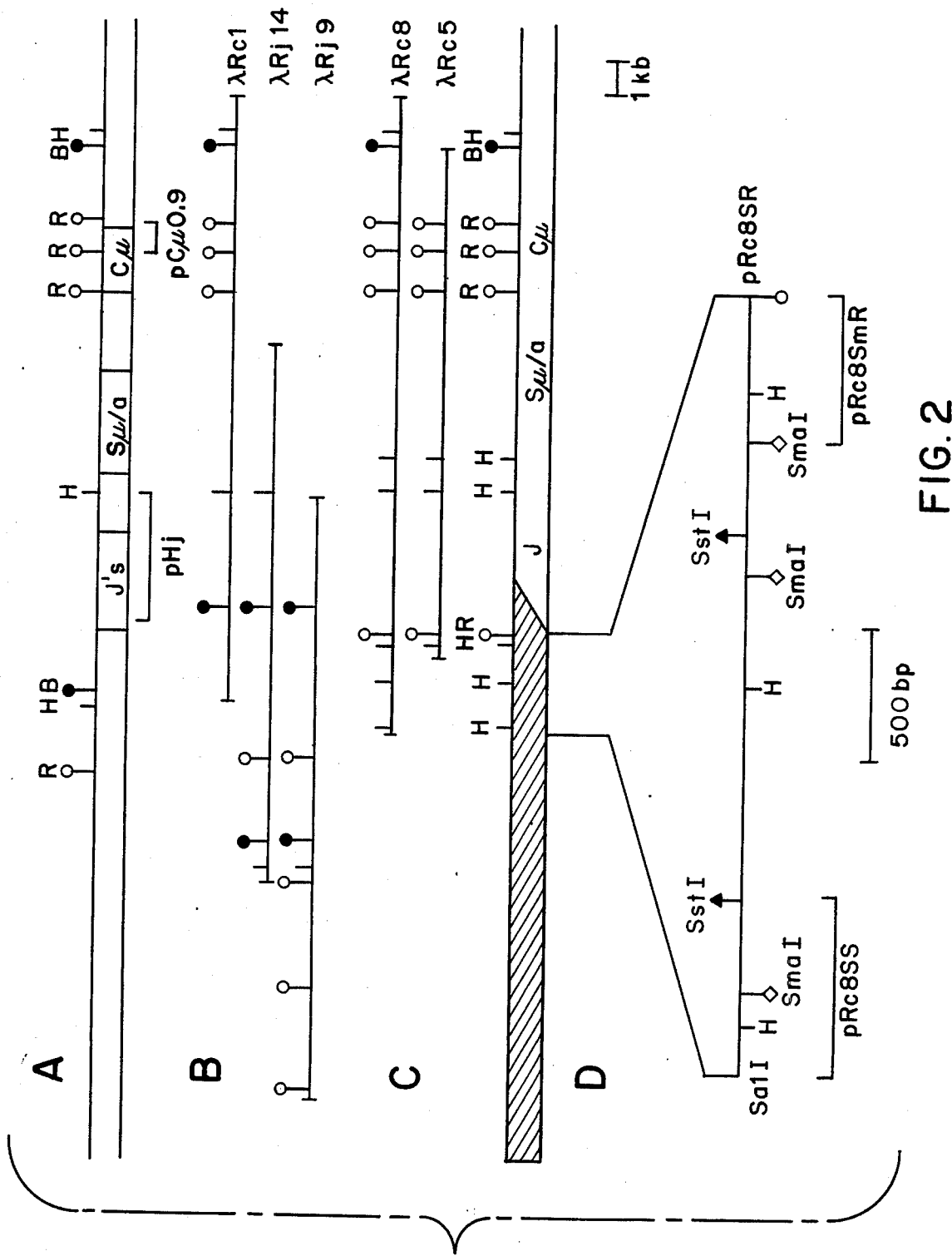
FIG. 2 shows restriction maps of the germ line C-mu gene (A), and of the two classes of recombinant clones obtained (B and C).

In a similar manner to that in Example 3, a full genomic library was prepared from the DNA of CLL 271 fresh leukemic cells of Example 2. After packaging in vitro, 375,000 independent recombinant phages were screened with the $pC_u$ 0.9 (a probe homologous to the immunoglobin $\mu$ chain of the C (constant) region containing a 0.9kbEcoR1 fragment) and the pHj probes. Ten clones were selected and restriction map analysis allowed classification into two groups that represented sequences derived from the uninvolved chromosome 14 and from the 14q+ hybrid chromosome. The restriction maps and representative overlapping recombinant clones of each group are shown in FIGS. 2B and C (H, Hind III; R. Eco RI; B. Bam. HI). The recombinant clones shown in FIG. 2B contain the shorter Bam HI fragment hybridizing with the pCu 0.9 or pHj probes and represent the productively rearranged u gene on the uninvolved chromosome 14. The other group, illustrated in FIG. 2C, represents the excluded $\mu$ allele on the 14q+ chromosome. As shown in FIG. 2, the restriction maps of the two groups, 5' of the $J_H$ segments, are completely different from each other and also from that of germ line DNA.

EXAMPLE 5

In order to establish which of the two groups of the recombinant clones derived from the 380 cell line contain the breakpoint between chromosomes 8 and 14 DNA fragments (p380j-2RR and p380j-9SS) 5' of both cloned $J_H$ segments (FIG. 2) that were free of repetitive sequences were subcloned using a pBR322 derivative in an *E. Coli* host. These subclones were then used as probes in Southern hybridization of DNA derived from human cells and Hind III digested DNA from rodent-$\times$human hybrid cells containing either human chromosome 8 or 14. DNA samples were fractionated on a 0.7% agarose gel. The Southern blot filter was hybridized in 50% formamide and 4 xSSC at 37° C. with $^{32}$P-labeled p380j-9SS probe and finally washed with 0.2 xSSC at 65° C.

Figure 3:
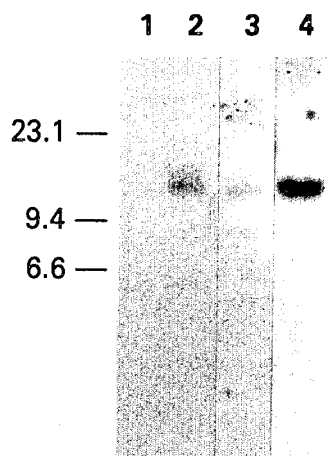
FIG. 3 depicts hybridization with the p380j-9SS probe of Hind III-digested DNAs from rodent X human hybrid cells containing human chromosome 8.

The results of this hybridization are shown in FIG. 3: lane 1, DNA from CHO (Chinese hamster ovary cell); lane 2, DNA from 706B6-40C1 17 (CHO$\times$human hybrid cell containing only human chromosome 8); lane 3, DNA from 280AG8Ce4 (mouse$\times$human hybrid containing human chromosome 8 but not human chromosome 14); lane 4, DNA from 545T human cell line. As shown in this figure, probe p380j-9SS hybridized with human DNA and with the DNA of a CHO$\times$human hybrid containing only human chromosome 8 and no other human chromosomes. The same probe did not hybridize with rodent$\times$human hybrids containing only human chromosome 14. Therefore, the class of recombinants containing the p380j-9SS DNA segment carry the joining region between chromosomes 8 and 14 on the 14q+ chromosome (FIG. 1).

As a control it was established the the p380j-9SS probe detected only a single germ line hybridizing fragment in the DNA of a T-cell line (545T) derived from the same patients from whom the leukemic 380 cell line was obtained, and also in DNAs derived from various other human cells. This probe, however, detected a germ line and a rearranged DNA fragment in the 380 leukemic cell line DNA indicating that the translocation between 8 and 14 occurred as a somatic event during the development of the patient's leukemia.

Since the p380j-9SS probe did not hybridize with DNA from chromosome 14, and since the pHj probe specific for the $J_H$ segment did not hybridize with the DNA segment on the left of the most 5' Hind III site of the clone lamda 380j-9 (FIG. 1) the chromosome 14 breakpoint involved in the t(8; 14) translocation was between the most 5 Sst I site and the second Hind III site as shown in FIG. 1C.

The p380j-2RR probe (FIG. 1B) was hybridized to DNA isolated from mouse×human and CHO×human hybrid cells containing human chromosomes 14 and 18 respectively. The probe hybridized with human DNA and with DNA derived from hybrids containing human chromosome 18, but not with DNA from hybrids containing human chromosome 14. Thus, clones 380j2 and 380j3 contain the joining region between chromosomes 14 and 18.

EXAMPLE 6

Figure 4:
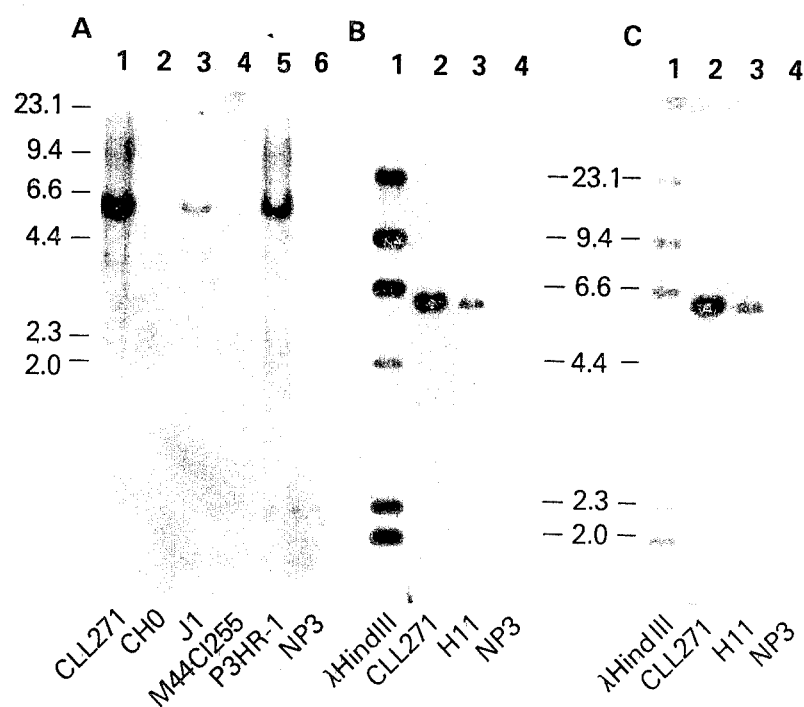
FIG. 4 shows hybridization of Eco RI digested human chromosome 11 containing rodent X human hybrid cell DNAs with sequence of pRc8SS and pRc8SmR.

To test whether the recombinant clones derived from the fresh leukemic cells, CLL 271, shown in FIG. 2C, contain the t(11; 14) breakpoint a single copy DNA sequence derived from chromosome 11 within the Lambda Rc8 and the Lambda Rc5 cloned DNAs (FIG. 2C) was isolated. The Sal I-Sst I fragment and a Sma I-Eco RI fragment pictured in FIG. 2D were subcloned into plasmid vectors pUC19 (Norrander et al, Vol. 26, p. 101 (1983)) and a derivative of pBR322 designated pYT13 (Tsujimoto and Suzuki) and replicated in *E. coli*. The subclones were designated pRc8SS and pRc8SmR, respectively (FIG. 3D). These two probes were used for hybridization with Southern blots of DNA from somatic cell hybrids between rodent cells and human cells that retained either human chromosome 14 or human chromosome 11. The results of this procedure are shown in FIG. 4.

Samples of five micrograms of DNA for (A) and ten micrograms for (B) and (C) were loaded on the gels. J1 cells are human chinese hamster ovary hybrids containing only human chromosome 11; H11 cells are human×mouse hybrids containing only human chromosomes 11 and Xq; and P3HR-1 cells are derived from a Burkitt lymphoma. Hybrid M44 (C12S5) is a human×mouse cell line containing only the human chromosome 14q+ from P3HR-1 Burkitt lymphoma, and NP3 cells are derived from a mouse myeloma cell line.

The DNA samples were digested with Eco RI and the Southern blot filters were hybridized with probe pRc8SS (lane A and B) and with pRc8SMR (lane C). The final washing of filters was done with 2×SCE at 65° C. for (A) and with 0.2×SSC at 65° C. for (B) and (C). The DNA of J1, H11 and CLL 271 cells showed the same size fragments (approx. 6kb) hybridizing with the two probes while mouse and Chinese hamster DNA did not hybridize with the probes. The pRc8SS probe did not hybridize with the DNA from hybrid cells containing human chromosome 14 (FIG. 5A, lane 4). Thus, the recombinant clones Lambda Rc8 and Lambda Rc5 contain the joining site between chromosomes 11 and 14 on the 14q+ chromosome of CLL 271 cells.

Because the Eco RI digest of CLL 271 DNA showed a single restriction fragment hybridizing with chromosome 11 DNA, which is the same as that observed in P3HR-1 Burkitt lymphoma cells with the t(8; 14) translocation (FIG. 4 A Lane 5), it can be inferred that the breakpoint on 14q$^{30}$ occurred in a region 3' to the most 5' Eco RI site of the Lambda Rc8 and Lambda Rc5 clones (FIG. 3).

EXAMPLE 7

DNAs of mouse×human and Chinese hamster×human hybrid cells containing chromosomes 14 and/or 18 were hybridized with the p380j-2RR probe (FIG. 1). DNA samples were digested with BamH1 and fractionated on a 0.7% agrarose gel. The Southern blot filter was hybridized with $^{32}$P-labeled p380j-2RR and washed as described above. The p380j-2RR probe hybridized with human DNA and with DNA derived from hybrids containing human chromosome 18, but not with DNA from hybrids containing human chromosome 14. These data indicate that clones 380j2 and 380j3 contain the joining region between chromosomes 14 and 18.

EXAMPLE 8

Figure 5:
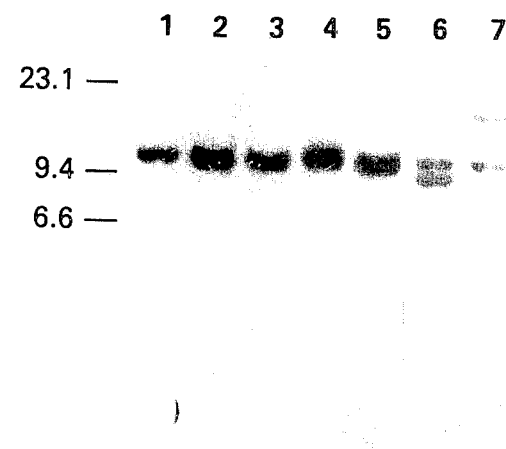
FIG. 5 is a southern blot hybridization with human chromosome 18-specific prolbe p380j-2RR of DNA from 380 leukemic cells and LN128 lymphoma cells.

The p380j-2RR chromosome 18 specific probe was hybridized with DNA from human cells of various origins and from 380 cells. Human DNAs were cut with Sst1 and run on a 0.7% agarose gel. The Southern blot filter was hybridized with $^{32}$P-labeled p380j-2RR and washed as described above. The results of this procedure are depicted in FIG. 5: lane 1, DNA EBV-transformed human lymphoblastoid cells; lane 2, DNA from a human T-cell lymphoma; lane 3, DNA from cells of CLL 271 (which carries a t(11; 14) chromosome translocation); lane 4 DNA from Burkitt lymphoma cell line (DAUDI) with t(8; 14) translocation; lane 5, DNA from 545T T-cell line; lane 6; DNA from 380 leukemic cell line; and lane 7, DNA from LN128 cells (human follicular lymphoma with the t(14; 18) chromosome translocation).

As shown in FIG. 5, all human DNAs tested except the DNA of the 380 and of the LN 128 neoplastic B cells which had an additional hybridizing fragment, showed a single hybridizing fragment representing the germ line sequence. A single germ line band in DNA from 545T-cell line (lane 5) was also detected. Therefore, the t(14; 18) translocation and the DNA rearrangement observed in FIG. 5, lane 6, occurred as a somatic event during the development of this leukemia.

EXAMPLE 9

DNA derived from the neoplastic cells of a 35 year old male diagnosed by standard methods as having follicular lymphoma (LN 128) exhibited both a germ line and a rearranged DNA fragment when hybridized with the p380j-2RR DNA probe (FIG. 5, line 7). The additional band of hybridization compared to the control lane (lane 1) indicates the presence of follicular lymphoma. A karyotypic analysis of this patient's chromosomes revealed a reciprocal t(14; 18) (q32; q21) translocation.

EXAMPLE 10

Probe pRc8SmR, specific for chromosome 11, was hybridized to DNAs isolated from various sources to detect rearranged fragments derived from hybrid chromosomes. Cellular DNA(5 ug) from various sources was digested with Hind III or BcII and fractionated by agarose gel electrophoresis. The Southern blot filter was hybridized with the pRc8SmR probe and finally washed with 0.2×SSC at 65° C. The DNA sources included: Molt 4 (human T-cell line) DNA, GM607 (human lymphoblastoid cell line DNA), Colo 320DM (human carcinoid) DNA, PAF (SV40 transformed human fibrobalst) DNA, HSB2 (human T-cell line) DNA, CLL 271 (human B-cell leukemia) DNA, LN87 (human B-cell lymphoma) DNA.

All human DNA samples tested, except for the CLL 271 DNA, exhibited hybridization to two Hind III fragments; the CLL 271 DNA exhibited one additional rearranged fragment. One of the Hind III fragments of approximately 2.5kb, represents the normal chromosome 11 sequence. This indicates that the chromosome break on 14q+ occurs within a region of 2.1kb 3' to the most 5' EcoR I site of Lambda Rc8 DNA (FIG. 2D).

The Bcl I digestion showed a rearranged fragment in LN87 cell DNA as well as in CLL 271 cell DNA. This result indicates that the breakpoint in LN 87 is close to the breakpoint observed in CLL 271 cells. The consistent location of the breakpoints in the case of CLL 271, a chronic lymphocytic leukemia, and LN 87, a diffuse large cell lymphoma, both having the t(11; 14) translocation, indicates the involvement of the same gene, putatively called bcl-1 (B-cell lymphoma/leukemia-1) in a variety of B-cell malignancies exhibiting this chromosomal translocation.

Since modifications will be apparent to those skilled in the art, it is intended that this invention be limited only by the scope of the appended claims.

I claim:

1. A method for diagnosing B-cell neoplasm associated with translocated chromosomes comprising:
    a. hybridizing a labeled DNA probe to restricted B-cell DNA, said DNA probe hybridizing to a region of DNA lying between a restriction site of a hybrid chromosome of a malignant B-cell and the breakpoint of said chromosome, said restriction site being unique to said region, said probe hybridizing to a chromosome selected from the group consisting of human chromosomes 11 and 18;
    b. identifying the pattern of restricted chromosomal DNA segments to which the DNA probe hybridizes; and
    c. detecting differences between the test pattern and the pattern for restricted normal chromosomal DNA.

2. A method for constructing a DNA probe for detecting malignant B-cells carrying a hybrid chromosome joined at a breakpoint, comprising:
    a. constructing a genomic library of DNA from said malignant B-cells;
    b. selecting clones containing DNA homologous to a region of chromosomal DNA spanning the breakpoint of the hybrid chromosome of said malignant B-cell; and
    c. subcloning DNA fragments containing DNA homologous to chromosomal DNA on only one side of said breakpoint, said DNA fragments hybridizing to a human chromosome selected from the group consisting of 11 and 18.

3. An assay for the detection of B-cell neoplasm associated with translocated chromosomes wherein lymphocyte DNA is tested for the presence of chromosomal translocations identified by a DNA probe by the steps comprising:
    a. removing lymphocytes from an individual and extracting chromosomal DNA therefrom;
    b. restricting said lymphocyte DNA;
    c. contacting said restricted DNA with a labeled DNA probe that hybridizes to a region of DNA of a chromosome lying between a restriction site of the chromosome and the breakpoint of a hybrid chromosome, said restriction site being unique to said region, said probe hybridizing to a chromosome selected from the group consisting of human chromosomes 11 and 18;
    d. identifying the pattern of restricted chromosomal DNA segments to which the DNA probe hybridizes; and
    e. detecting differences between the test pattern and the pattern for restricted normal chromosomal DNA.

4. The assay of claim 3 wherein the probe hybridizes to human chromosome 18.

5. The assay of claim 3 wherein the probe hybridizes to human chromosome 11.

6. The method of claim 2 wherein the malignant B-cells were isolated from a follicular lymphoma patient.

7. The method of claim 2 wherein the malignant B-cells were isolated from a B-cell malignancy selected from the group consisting of chronic lymphocytic leukemia and diffuse B-cell lymphoma.

* * * * *